US005450629A

United States Patent [19]
Gilstrap

[11] Patent Number: 5,450,629
[45] Date of Patent: Sep. 19, 1995

[54] CONVERTIBLE HAT WITH A FOLDABLE VISOR AND ASSOCIATED METHOD

[76] Inventor: Keith D. Gilstrap, 523 E. Ave., Rifle, Colo. 81650

[21] Appl. No.: 182,733

[22] Filed: Jan. 14, 1994

[51] Int. Cl.⁶ ............................................... A42B 1/20
[52] U.S. Cl. ........................................ 2/209.11; 2/10; 2/12; 2/195.1; 2/195.2; 2/209.12; 383/4
[58] Field of Search .................. 2/171, 10, 12, 171.03, 2/183, 175.1, 195.1, 195.2, 195.3, 195.4, 209.11, 209.12, 417, 418, 420; 383/4

[56] References Cited

U.S. PATENT DOCUMENTS

| | | |
|---|---|---|
| 625,776 | 5/1899 | Von Klein . |
| 1,213,447 | 1/1917 | Bacon . |
| 1,269,594 | 6/1918 | Geraghty ............................... 2/171 |
| 1,718,867 | 6/1929 | Mahlmann ............................ 2/12 |
| 1,732,357 | 10/1929 | Davis . |
| 2,057,915 | 10/1936 | Probst .................................. 2/195.1 |
| 2,158,861 | 5/1939 | Meyer . |
| 2,493,500 | 1/1950 | Rankin . |
| 2,765,472 | 10/1956 | Schoen-Wolski . |
| 2,766,458 | 10/1956 | Schoen-Wolski . |
| 2,896,218 | 7/1959 | Lipschutz . |
| 3,039,113 | 6/1962 | Lipschutz . |
| 3,285,307 | 11/1966 | Dormaier ............................. 2/209.11 |
| 3,370,304 | 2/1968 | Pelletier ............................... 2/195.2 |
| 4,549,316 | 10/1985 | Johnson . |
| 4,682,373 | 7/1987 | Baran . |
| 4,694,506 | 9/1987 | Perna . |
| 4,839,924 | 6/1989 | Laurence ............................. 2/10 |
| 5,214,802 | 6/1993 | McCallum .......................... 2/209.12 |
| 5,303,427 | 4/1994 | Fishbaine ............................ 2/171 |
| 5,381,559 | 1/1995 | Wakefield, III .................... 2/195.1 |

FOREIGN PATENT DOCUMENTS

| | | | |
|---|---|---|---|
| 644095 | 4/1937 | Germany ............................. 2/12 |
| 258570 | 5/1949 | Switzerland ......................... 2/12 |

Primary Examiner—Clifford D. Crowder
Assistant Examiner—Diana L. Biefeld
Attorney, Agent, or Firm—Lee R. Osman; Holland & Hart

[57] ABSTRACT

A hat has a shell of general hemispherical shape with an open bottom, a peripheral edge around the open bottom and an interior. A visor, having an inside edge and an outside edge, is flexibly attached along a section of the peripheral edge to the shell and extends substantially perpendicularly away from the shell. The visor has a plurality of fold lines extending from its inside edge to its outside edge. The fold lines allow the visor to be folded to a reduced size and tucked into the interior of the hat to form a purse.

12 Claims, 4 Drawing Sheets

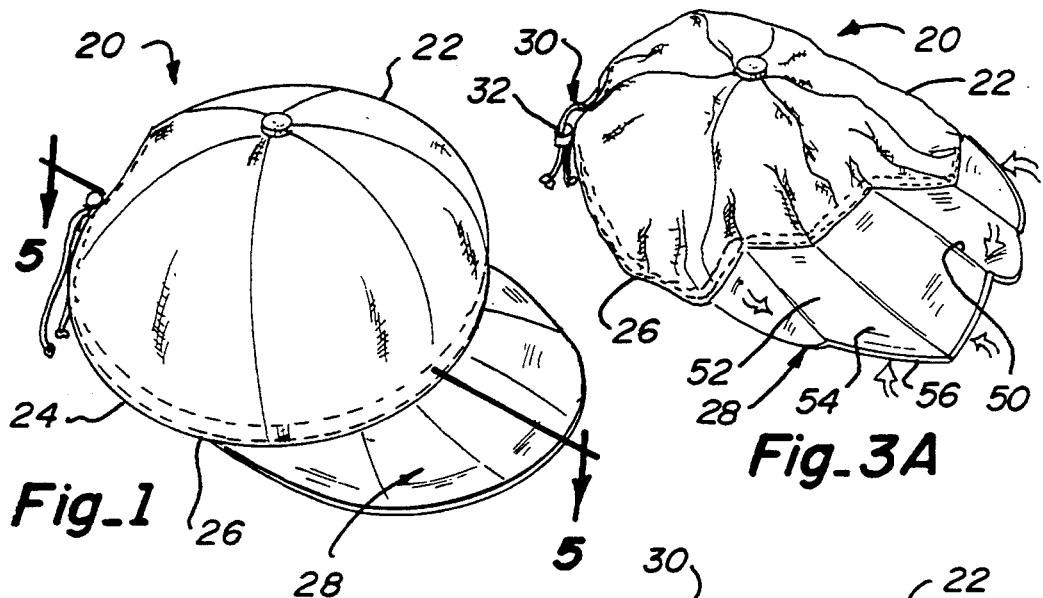
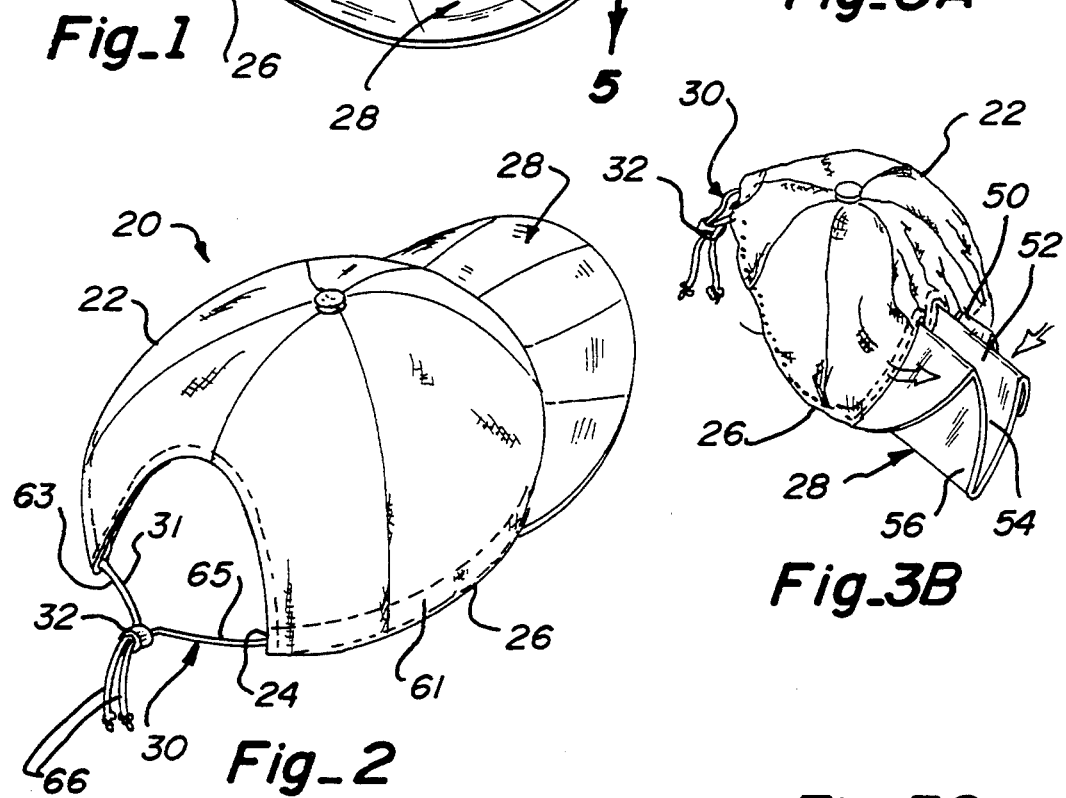
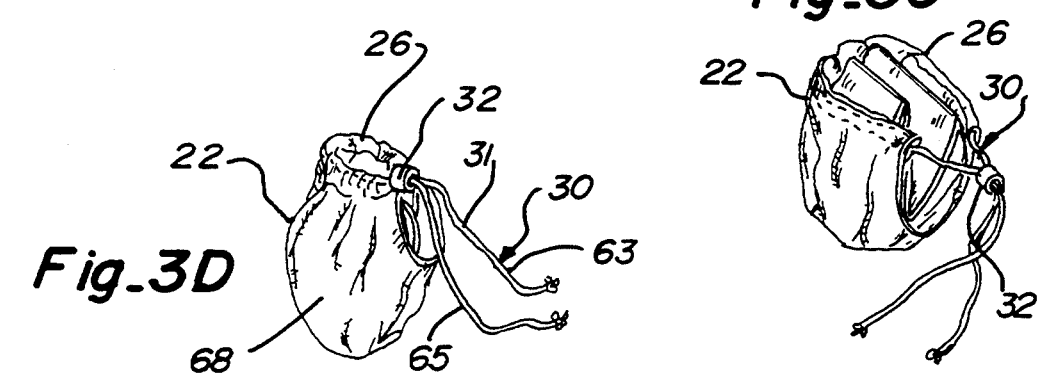

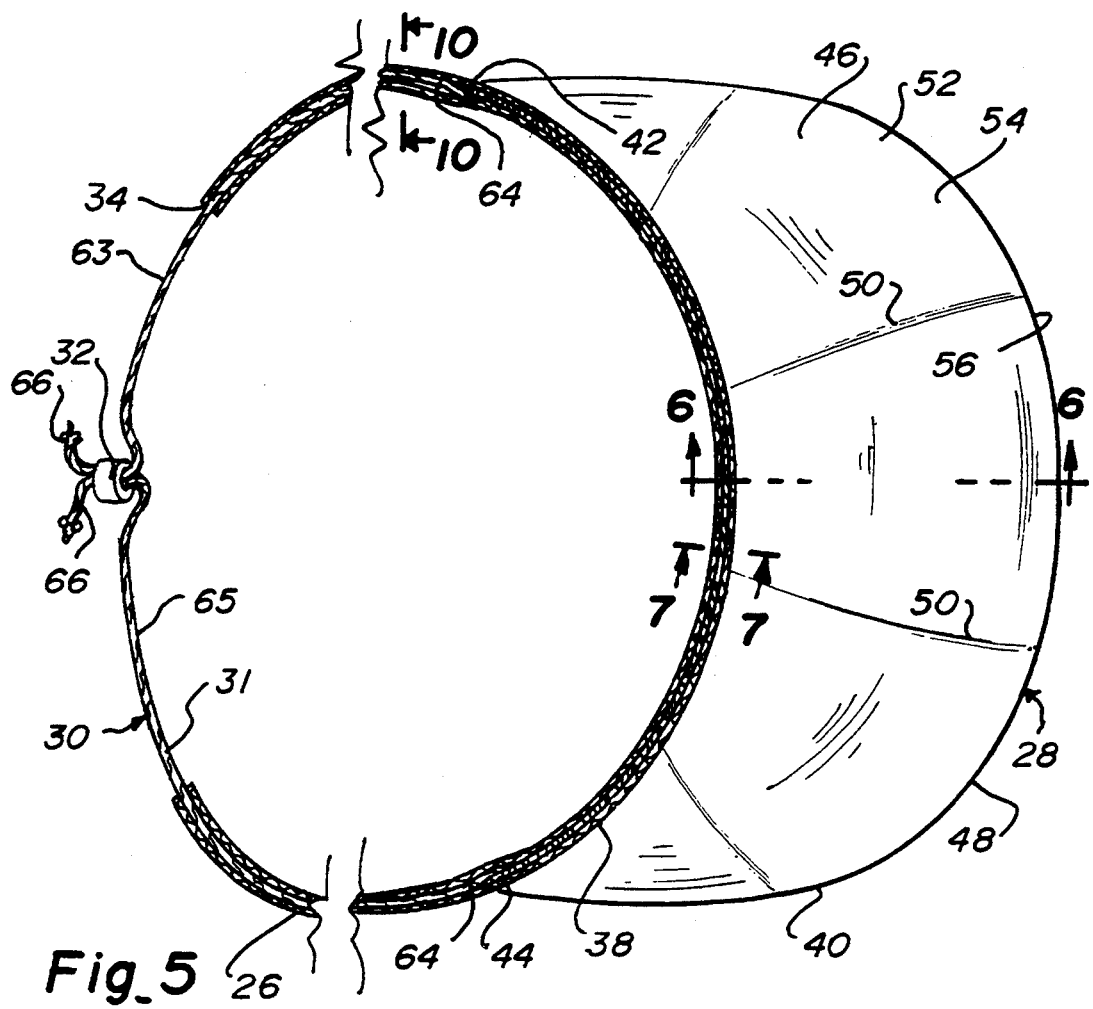
Fig_5
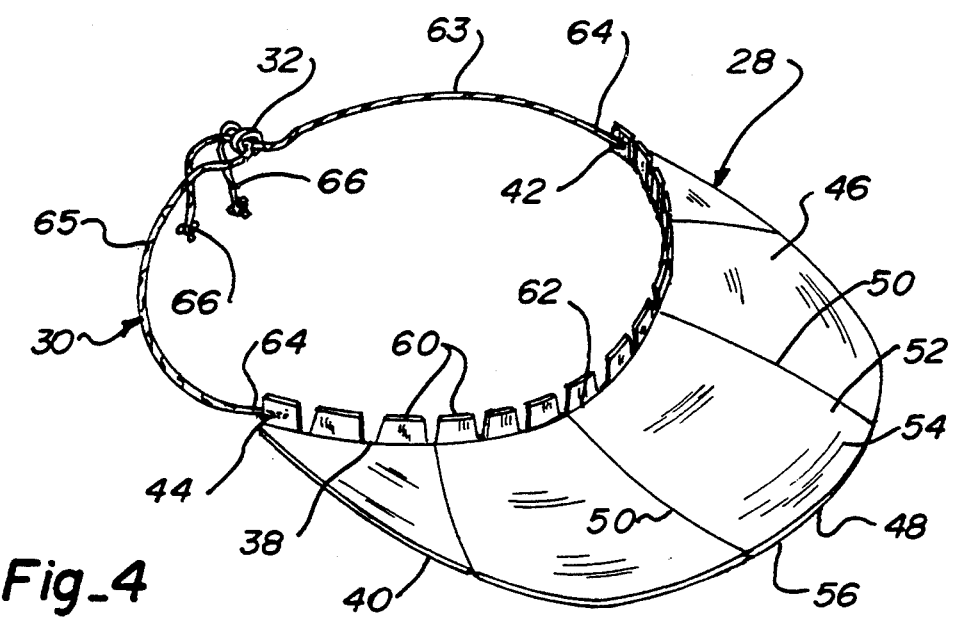
Fig_4

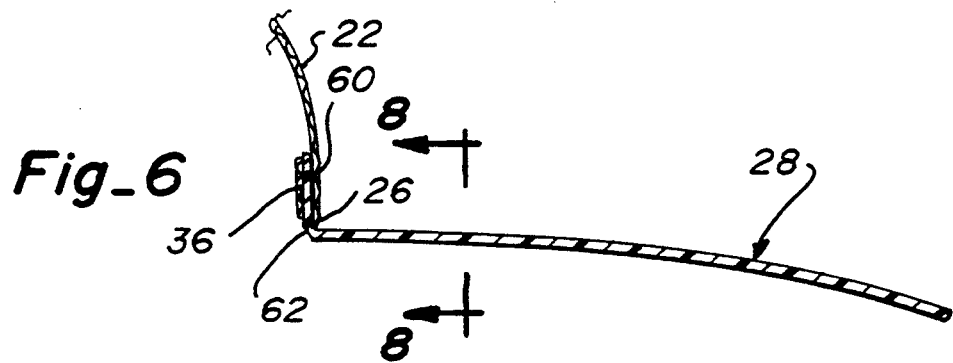
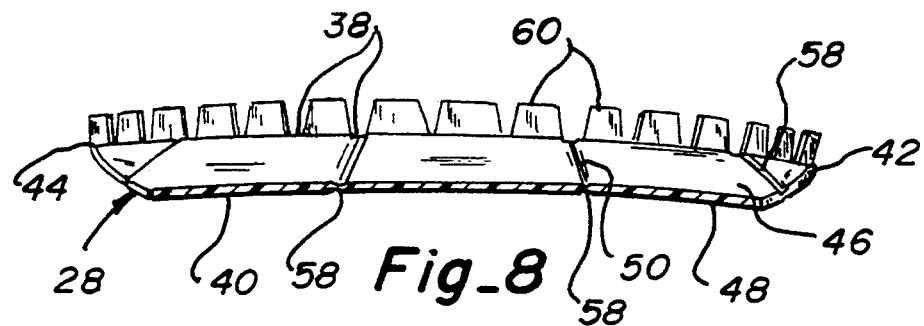
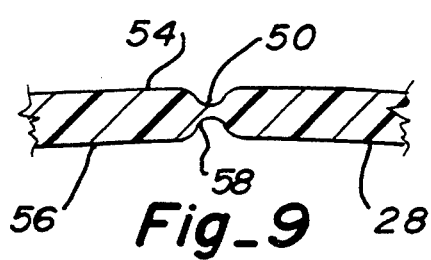
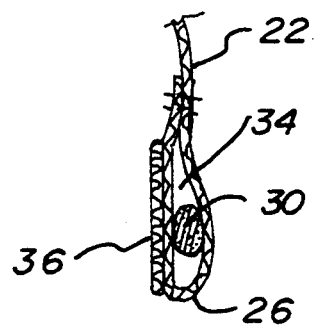
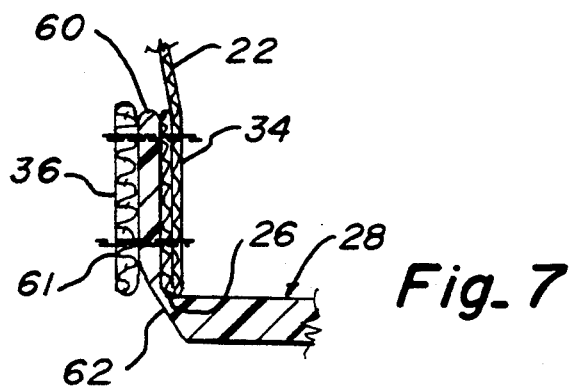

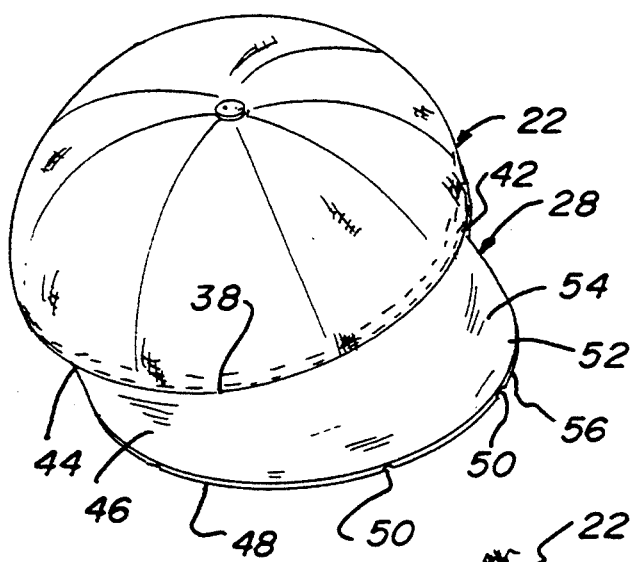
Fig_11
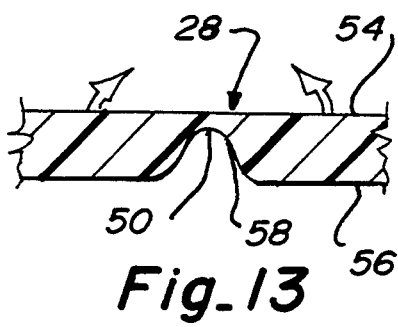
Fig_13
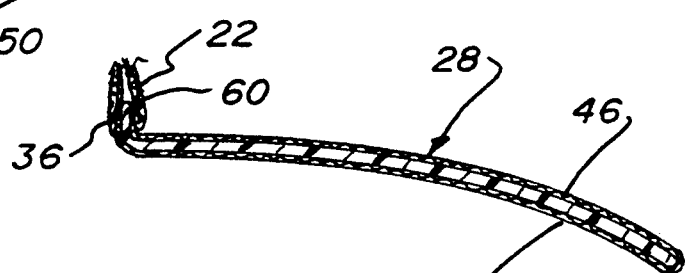
Fig_12

CONVERTIBLE HAT WITH A FOLDABLE VISOR AND ASSOCIATED METHOD

BACKGROUND OF THE INVENTION

1. Field of the Invention

This invention relates to a new and improved hat, and more particularly to a hat with a foldable visor which can be tucked into the shell of the hat and wherein the hat includes a draw string around the perimeter of the shell to convert the hat to a purse when the visor is tucked in the shell.

2. Description of the Prior Art

Hats have been used for many years and are found in many shapes and sizes. Hats are used as sun shades, to repel the weather and often simply for aesthetic purposes. A popular hat is the baseball-style cap. The baseball cap typically comprises a shell, a visor attached to an edge of the shell to shade the user, and an adjustment system along the edge of the shell to allow for changing the size of the hat. The shell is typically made of a flexible material. The visor is typically made of a rigid material and extends substantially perpendicularly away from the shell to provide shade for the user's face.

When hats are worn for any of their many uses, the user often desires to remove the hat but keep the hat available for later use. If the user is participating in an activity at the time he takes the hat off, such as hiking or other sports, conveniently storing the hat for later use can pose a significant problem.

Most hats must simply be carried by hand or in some type of carrier when not in use. Carrying a hat by hand subjects the hat to damage from exposure to dirt or physical damage such as being crushed or otherwise deformed. Using a carrier for a hat is inconvenient for the active user. Storing hats while not in use is a recognized problem, indicated by the numerous attempts by inventors to provide a hat that is conveniently storable and portable.

Attempts to create hats that are able to be reduced to a convenient size have concentrated on rolling the hats into a roll, folding visors in one or a plurality of locations, and also folding both the visor and the shell together. U.S. Pat. No. 1,213,447 issued to R. H. Bacon in 1917 discloses a visor made up of separate sections held together by pliable hinge strips. The visor is foldable to a reduced size, but still must be placed somewhere for storage, and provides no extra functionality when in its reduced size.

U.S. Pat. No. 625,776 issued to C. H. Von Klein in 1899 discloses a hat that has a foldable body and a visor that is hinged at one place to fold over on itself. While the hat is able to be reduced in size, the shape of the hat in its reduced size is as difficult to store as the hat in its normal state.

U.S. Pat. No. 1,718,867 issued to S. Mahlmann in 1926 provides a hat with a foldable eyeshade that extends down over the user's eyes. The visor is foldable but the rest of the hat must simply be folded in any manner with the visor for storage.

U.S. Pat. No. 2,158,861 issued to M. Meyer in 1937 discloses a hat where the body is foldable but the visor remains in a rigid crescent shape. The size of the hat when folded is smaller than when in use, but the rigid visor impedes the adequate reduction of size necessary for convenient storage.

U.S. Pat. No. 2,493,500 issued to E. Rankin in 1947 discloses a fedora style hat that has a diagonally foldable body. When in its folded position, the height of the hat is reduced but the overall size of the hat is not substantially changed.

U.S. Pat. No. 2,765,472 issued to W. Schoen-Wolski provides a hat where both the visor and body are foldable and are reduced into a long strip of material. The result is a peculiar looking hat with no functionality in its reduced size.

U.S. Pat. No. 4,549,316 issued to Johnson in 1985 provides a baseball cap with a visor that is foldable only along its centerline. The shell of the hat is not reduced in size, and is presumably left to be exposed to dirt and physical damage when the folded bill is placed in the user's back pocket.

U.S. Pat. No. 4,682,373 issued to Baran in 1987 provides a fedora style hat that is able to be rolled up for storage purposes. As with all of the other inventions, this invention provides no means to store the hat, or to provide portability once the hat is reduced in size and stored.

U.S. Pat. No. 4,694,506 issued to Perna in 1987 discloses an eyeshade made of a visor and a separate head band connected by tape that is able to be folded and stored in one's purse or pocket. The eyeshade is complicated and provides no extra functionality when in its folded position.

Hats that are foldable have a similar problem as hats that are not foldable in that once they are folded they must be placed somewhere for easy storage and provides for convenient portability. None of the attempts has resulted in a hat that is able to be reduced in size for convenient storage and portability.

In addition, the structural modifications that make folding the hat possible also detrimentally affect the aesthetics of the hat when in use. The differences are seen in the visor of the hat, where folds and creases are conspicuously apparent.

Another concern in the use of storable hats is that once the hat has been reduced to its smaller size for storage, it no longer provides any useable function. The hat, when folded and ready for storage, is only an article to place somewhere; it has no function of its own.

The problems of making a hat convertible to a conveniently carried form, providing a way to carry the hat once it is reduced to its smaller size, and providing a hat with functionality when in its storable form have not been successfully resolved. It is to overcome these shortcomings in the prior art that the present invention was developed.

SUMMARY OF THE INVENTION

The present invention in general terms concerns a hat which is convertible to an easily storable form, and more particularly to a hat having a foldable visor that can be tucked into the shell which forms a purse in which other small items can be stored with the attached visor.

The hat of the present invention provides functionality that overcomes the afore-mentioned problems. The hat has a foldable visor which is storable within the shell of the hat itself forming a small, convenient and secure method to reduce the size of the hat and increase its utility when not being worn on the user's head.

The hat of the present invention functions as any other hat when worn. The size of the hat, however, can be adjusted by means of a drawstring system around the perimeter of the shell of the hat which makes the hat infinitely adjustable for most head sizes. The drawstring system also acts as a closure for the hat once the visor has been folded and tucked into the shell. The drawstring can draw tight around the perimeter of the shell after the visor has been folded and tucked into the shell, providing a purse in which small items can be carried.

When the hat is not in use, it is reduced to its smaller size by folding the visor along fold lines, tucking the folded visor inside the shell of the hat and then tightening the drawstring to convert the shell of the hat into a purse. After the hat is formed into a purse, it can be used to carry any other article that will fit into the purse. The hat, in the folded form, can also be attached by the drawstring to an object for convenient storage or portability.

The hat, while in use, shows little indication it is any different than a non-foldable hat. The visor has a substantially smooth curve with little indication it is foldable.

Accordingly, it is a primary object of the present invention to provide a hat that is readily reduced to a smaller size for convenient storage and portability.

It is another object of the present invention to provide a hat that, when reduced to a smaller size for storage and portability, serves to carry other objects if so desired.

Still another object of the present invention is to provide a hat that is readily storable and portable yet has a substantially smooth visor when in use.

Yet another object of the present invention is to provide a hat with a foldable visor that is storable within the shell of the hat.

Other aspects, features and details of the present invention can be more completely understood by reference to the following detailed description of a preferred embodiment, taken in conjunction with the drawings, and from the appended claims.

BRIEF DESCRIPTION OF THE DRAWINGS

FIG. 1 is an isometric view of the hat of the present invention from a front angle, illustrating a visor, a shell, and a drawstring system.

FIG. 2 is an isometric view of the hat shown in FIG. 1 from a rear angle illustrating the drawstring system at the rear of the hat.

FIGS. 3A-3D are operational isometric views showing separate phases of converting the hat shown in FIG. 1 to a purse.

FIG. 4 is an isometric view of the visor and drawstring components of the hat shown in FIG. 1.

FIG. 5 is a section taken along line 5—5 of FIG. 1, illustrating the visor and drawstring system including the head liner and hem of the hat.

FIG. 6 is a section taken along line 6—6 of FIG. 5, illustrating the headlining, sew-tabs, shell and visor of the present invention.

FIG. 7 is an enlarged section taken along line 7—7 of FIG. 5.

FIG. 8 is a section taken along line 8—8 of FIG. 6.

FIG. 9 is an enlarged fragmentary section taken through the visor of the hat showing the specific structure of a fold line.

FIG. 10 is an enlarged section taken along line 10—10 of FIG. 5.

FIG. 11 is an isometric view of an alternative embodiment of the hat of the present invention.

FIG. 12 is a vertical section of the visor of a hat of the present invention illustrating a cloth material covering on the visor.

FIG. 13 is a an enlarged section taken along line 13—13 of FIG. 11, showing an alternative structure of a fold line in the visor.

DESCRIPTION OF THE PREFERRED EMBODIMENT

Referring first to FIG. 1 the convertible hat 20 of the present invention is illustrated and includes a shell 22 having a general hemispherical shape with an open bottom 24 defining a peripheral edge 26 around the opening 24, a visor 28 operably attached along a section of the peripheral edge 26 of the shell 22, and a drawstring system 30 also attached along a section of the peripheral edge 26 of the shell 22, including a drawstring 31 and a fastener 32. A rear view of the present invention is shown in FIG. 2, wherein free ends 66 of the drawstring 31 are shown extending from the peripheral edge 26 of the shell 22 at the rear of the hat 20. The fastener 32 is operably attached to the free ends 66 of the drawstring 31 to allow adjustment of the drawstring system 30.

The convertible hat 20, when being worn, functions as any other baseball style hat. The user puts the hat 20 on his/her head, with the visor 28 normally extending outwardly over the user's face, and adjusts the size of the hat for a comfortable fit. At this point the unique features of the hat 20 of the present invention become apparent. The size of the hat 20 is infinitely adjustable to nearly any head size because the size is adjusted continuously by use of the drawstring system 30. When the user desires to remove the hat 20 but keep it available for later use, the other unique features of the hat are able to be exercised, as is discussed in substantial detail below.

Regarding the shell 22, the peripheral edge 26 is hemmed, defining a channel 34 extending around the entire peripheral edge 26 of the shell 22, as shown in FIGS. 5, 7, and 10. A head liner 36 is operably attached along the inside of the peripheral edge 26 of the shell 22 to help provide a comfortable fit for the user, as shown in FIGS. 5, 7, and 10.

The visor 28 as shown in FIGS. 4, 5, and 8, is crescent shaped, having an inner edge 38, an outer edge 40, a first end 42 and a second end 44. The visor also has a top side 46 and a bottom side 48. The inner edge 38 of the visor 28 has a curvature that is substantially the same as the curvature of the peripheral edge 26 of the shell 22. The outer edge 40 of the visor 28 is curved so that the inner edge 38 and the outer edge 40 intersect at the two ends 42 and 44 of the visor 28. The dimension between the two edges 38 and 40 is a maximum at a distance halfway between the two ends 42 and 44, and uniformly decreases toward each of the two ends, thus forming a substantially flat crescent shape. The visor 28 as shown in FIG. 8 has an arcuate transverse cross-section from side to side which is useful for maintaining the visor 28 in a substantially smooth form when in use. The visor 28 is made of either a resilient material by itself, as shown in FIG. 6, or the same material with a fabric covering on both the top and bottom sides, 46 and 48, respectively, as shown in FIG. 12.

Referring to FIGS. 4, 5 and 11, a plurality of fold-lines or living hinges 50 are shown extending between the inner edge 38 and outer edge 40 of the visor. The fold-lines 50 allow the visor 28 to be folded to reduce the size of the hat 20 for convenient storage and portability. The fold-lines are evenly spaced. The fold-lines separate the visor into individual segments 52, each having a top face 54 and a bottom face 56. The fold-lines 50 are formed by continuous opposing indentations 58 along the top and bottom faces 54 and 56, respectively, of the visor 28 in a linear manner between the inner edge 38 and outer edge 40 of the visor 28, as shown in FIGS. 8 and 9. In a second embodiment the fold-lines 50 are formed by continuous indentation 58 in a linear manner between the inner 38 and outer 40 edges of the visor 28, but only on the bottom side 56 of the visor 28, as shown in FIG. 13. When the hat 20 is being used, the fold-lines 50 are noticeable but not conspicuously so.

The fold-lines 50 act as hinges between each segment, allowing the visor 28 to collapse from a laterally extended position while in use, as shown in FIG. 1, to a folded compact position for convenient storage and portability, as shown in FIG. 3.

A plurality of sew-tabs 60 extend substantially perpendicularly upwardly along the inner edge 38 of the visor 28, as shown in FIG. 4. The sew-tabs are used in attaching the shell 22 of the present invention to the visor. Each of the sew-tabs 60 are separate from one another, and each is integrally formed with the visor, as in FIG. 7. The area of connection between the sew-tabs and the visor forms a living hinge 62, as seen in FIG. 7, which allows the sew-tabs to pivot with respect to the shell 22 of the visor about the living hinge. The fold-lines 50 intersect the inner edge 38 of the visor 28 at locations between the sew-tabs to eliminate any interference caused by the sew-tabs in folding the visor, as seen in FIGS. 4 and 8.

Referring to FIGS. 6 and 7, the connection between the shell 22 of the present invention and the visor 28 is illustrated. The visor is operably connected along a section of the peripheral edge 26 of the opening of the shell 22. The sew-tabs 60 are positioned adjacent to, and along the inside peripheral edge of the shell 22. The shell, the sew-tabs and the head lining are connected together by any typical means, for instance by a sewing stitch 61 continuous along the section of the peripheral edge 26 to which the visor 28 is attached.

Referring to FIGS. 4 and 5, the relationship of the drawstring system 30 with the visor 28 is illustrated. The drawstring 31 comprises two separate elongated sections 63 and 65, each with a first end 64 and a second free end 66. The first end 64 of each one of drawstring sections 63 and 65 is operably attached to the outermost sew-tab 60 at either of the ends 42 or 44 of the inner edge 38 of the visor, as shown in FIG. 4. The second ends 66 of each of the drawstring sections 63 and 65 are operably connected by an adjustable fastener 32, as shown in FIG. 5.

When the visor 28, shell 22 and drawstring system 30 are related as shown in FIG. 1, each drawstring section 63 and 65 is slidably disposed within the channel 34 along the peripheral edge 26 of the shell 22 between where the drawstring section is attached to the sew-tab 60, and where it is attached to the second free end 66 of the other one of the drawstring sections, as shown in FIGS. 5 and 10. In this relationship, the drawstring system 30 can act to operatively shorten the peripheral edge 26 of the shell 22, as is necessary to form a purse 68, as seen in FIG. 3-D.

In operation of the present invention, in which the hat 20 is reduced in size for convenient storage and portability, the features described above will be more greatly appreciated. Referring to FIGS. 3-A through D, in reducing the size of the hat 20, the visor 28 is first folded along the fold-lines 50 into a compact form. When folded, the individual segments 52 of the visor are alternately folded upwardly and downwardly, in accordion style, such that the top faces 54 abut and are adjacent to one another while the bottom faces 56 abut and are adjacent to one another. In this manner the visor 28 can obtain a sufficiently reduced size adequate for insertion into the shell 22, as shown in FIG. 3-E. Since the fold-lines 50 intersect the inner edge 38 of the visor 28 between sew-tabs 60, the sew-tabs 60 do not interfere with folding the visor 28.

Once folded, the visor 28 is tucked inside the shell 22, made possible by the living hinge 62 between each of the plurality of sew-tabs 60 and the inner edge 38 of the visor 28. Once the folded visor 28 is tucked inside the shell 22, as shown in FIG. 3-C, the movable fastener 32 connecting the second free ends 66 of each of the drawstrings sections 63 and 65 is adjusted to effectively shorten the operative length of each of the drawstring sections. Shortening the operative length of each of the drawstring sections closes the opening 24 of the shell 22 by shortening the peripheral edge 26 of the shell 22, as shown in FIG. 3-D.

At this point, the hat 20 is fully reduced in size and has been converted into a purse 68 which holds the visor of the hat 20, as shown in FIG. 3-D. The purse 68, however, can also be used to carry any other item or items small enough to be placed within the inside of the shell 22 after the hat 20 is converted into the purse 68.

Numerous advantages accrue from the use of the convertible hat 20. The hat 20 is easily reduced in size for convenient storage. The hat of the present invention also provides convenient portability in the fact that the hat is self-contained once it is in its reduced size with the folded visor 28 inside the shell 22 and the drawstring system 30 tightened around the peripheral edge 26. The converted hat 20 can thus be carried by hand or tied, using the drawstring sections 63 and 65, to any convenient location to be carried with the user. Because the hat 20 is easy to fold and store, the hat 20 can be kept available for future use by the user when desired. The present invention provides a further improvement because it has the ability to carry items after the hat is converted into the purse 68. In this way, the hat 20 is not only able to be reduced in size for convenient storage and portability, but also has an added function of containing and carrying items which fit inside the shell 22 of the hat 20 after it is formed into a purse 68.

Although the present invention has been described with a certain degree of particularity, it is understood that changes in detail or structure may be made without departing from the spirit of the invention, as defined in the appended claims.

I claim:
1. A hat comprising:
a) a shell of general hemispherical shape having an open bottom defining a peripheral edge around said open bottom and an interior;
b) a visor flexibly attached along said peripheral edge and extending substantially perpendicularly away from said shell, said visor having an inside edge attached to the periphery of said shell and an outside edge; and
c) said visor having a plurality of fold lines extending substantially perpendicularly from said peripheral edge and extending from said inside to said outside edge, to facilitate said visor being folded in an accordion style along said fold lines and tucked into said interior of said shell.

2. The hat of claim 1 further comprising a head liner operably attached to said interior of said shell along said peripheral edge.

3. The hat of claim 1 wherein said visor has an arcuate transverse cross-section to bias said visor into an unfolded position.

4. The hat of claim 1 wherein said visor includes a plurality of flexible sew-tabs integrally formed along said inside edge of said visor and defining outermost sew-tabs, said sew-tabs extending substantially at right angles to said visor when said visor is unfolded, and the intersection of said tabs and said inside edge of said visor forming a living hinge to facilitate folding said visor into said interior of said shell.

5. The hat of claim 4, further comprising:
a) an elongated drawstring system operably attached to said visor, said visor having opposing first and second ends, and wherein said drawstring system is operably connected to said shell along said peripheral edge;
b) said drawstring system including a drawstring and a fastener for operatively adjusting the length of said drawstring, said drawstring having two sections, each having a first end and a second end, said first end of each of said two drawstring sections being operably attached to said visor at one of said first end or second end of said visor;
c) said shell having a channel along said peripheral edge, said drawstring sections being slidably disposed within said channel;
d) said second ends of each of said drawstring sections extending from said channel and being operably connected together by said fastener; and
e) said fastener being adjustable in said drawstring system to operatively shorten said peripheral edge to substantially close said open bottom of said shell.

6. The hat of claim 5, wherein said first end of each of said two drawstring sections are operably attached to said outermost sew-tabs at one of said first end or second end of said visor.

7. The hat of claim 1, wherein:
a) said visor has a top surface and a bottom surface; and
b) said plurality of fold lines comprise continuous aligned linear indentations along said top surface and bottom surface.

8. The hat of claim 1, wherein:
a) said visor has a top surface and a bottom surface; and
b) said plurality of fold lines comprise continuous linear indentations along said bottom surface.

9. The hat of claim 1 wherein said visor is made of a resilient material.

10. The hat of claim 1, wherein:
a) said visor has a top surface and a bottom surface;
b) said visor is made of a resilient material; and
c) said visor has a cloth material covering on said top surface and said bottom surface.

11. A method for converting a hat having a hemispherical shape with an open bottom defining a peripheral edge around said open bottom and an interior, a visor having an inner edge and outer edge flexibly attached along said inner edge to said peripheral edge and being extendable substantially perpendicularly away from said shell, said visor having a plurality of fold lines extending from said inside edge to said outside edge, a drawstring system operably connected to said peripheral edge having an adjustable operative length, into a purse, comprising the steps of:
a) folding said visor from a laterally extended position along the plurality of fold lines into a folded position;
b) tucking said folded visor through the open bottom into the interior; and
c) shortening the operative length of said drawstring system around the peripheral edge to act to close the open bottom and form the purse.

12. A hat comprising:
a) a shell of general hemispherical shape having an open bottom defining a peripheral edge around said open bottom and an interior;
b) a visor flexibly attached along said peripheral edge and extending substantially perpendicularly away from said shell, said visor having an inside edge connected to the peripheral edge of said shell, an outside edge, a first end and a second end, and a plurality of fold lines extending perpendicularly from said peripheral edge, and extending from said inside edge to said outside edge;
c) an elongated drawstring system operably attached to said visor and operably connected to said shell along said peripheral edge;
d) said drawstring system including a drawstring and a fastener for operatively adjusting the length of said drawstring, said drawstring having two sections, each having a first end and a second end, said first end of each of said two drawstring sections being operably attached to said visor at one of said first end or second end of said visor;
e) said shell having a channel along said peripheral edge, said drawstring sections being slidably disposed within said channel;
f) said second ends of each of said drawstring sections extending from said channel and being operably connected together by said fastener;
g) said fastener being adjustable in said drawstring system to operatively shorten said peripheral edge to substantially close said open bottom of said shell; and
h) said visor being foldable along said fold lines so that it can be tucked into the interior of said shell and retained therein by adjusting said fastener to close said open bottom.

* * * * *